United States Patent
Rhodes

(10) Patent No.: US 10,723,970 B2
(45) Date of Patent: Jul. 28, 2020

(54) FRAGRANCE COMPOSITIONS CONTAINING NORBORNENE DERIVATIVES

(71) Applicant: PROMERUS, LLC, Brecksville, OH (US)

(72) Inventor: Larry F Rhodes, Brecksville, OH (US)

(73) Assignee: PROMERUS, LLC, Brecksville, OH (US)

( * ) Notice: Subject to any disclaimer, the term of this patent is extended or adjusted under 35 U.S.C. 154(b) by 0 days.

(21) Appl. No.: 16/512,567

(22) Filed: Jul. 16, 2019

(65) Prior Publication Data
US 2020/0017799 A1    Jan. 16, 2020

Related U.S. Application Data

(60) Provisional application No. 62/698,453, filed on Jul. 16, 2018.

(51) Int. Cl.
| | |
|---|---|
| *C11B 9/00* | (2006.01) |
| *C11D 9/44* | (2006.01) |
| *A61L 9/01* | (2006.01) |
| *A61K 8/31* | (2006.01) |
| *A61K 8/37* | (2006.01) |
| *A61K 8/33* | (2006.01) |
| *A61K 8/34* | (2006.01) |
| *A61Q 19/00* | (2006.01) |

(52) U.S. Cl.
CPC .............. *C11B 9/0046* (2013.01); *A61K 8/31* (2013.01); *A61K 8/33* (2013.01); *A61K 8/34* (2013.01); *A61K 8/37* (2013.01); *A61L 9/01* (2013.01); *A61Q 19/007* (2013.01); *C11D 9/442* (2013.01)

(58) Field of Classification Search
CPC ......... C11B 9/0046; C11D 9/442; A61L 9/01; A61Q 19/007; A61K 8/37; A61K 8/33; A61K 8/34; A61K 8/31
USPC ...................................................... 514/785
See application file for complete search history.

(56) References Cited

U.S. PATENT DOCUMENTS

| | | | |
|---|---|---|---|
| 4,119,577 A | * 10/1978 | Light | .................. A24B 15/345 131/275 |
| 4,221,679 A | 9/1980 | Willis et al. | |
| 2013/0096175 A1 | 4/2013 | Goldfarb et al. | |

FOREIGN PATENT DOCUMENTS

DE     3443536 A1 *  5/1986  ............. C07C 33/12

OTHER PUBLICATIONS

DE-3443536-A1 Specification (English translation) (Year: 1986).*
M. K. Mamedov, Russian Journal of Organic Chemistry, (1998), p. 178-182 (English).*
Mamedov M. K., et al., "Ester Synthesis by Addition of Monocarboxylic Acids to exo-5-Substitued Bicyclo[2.2.1]hept-2-ene Hydrocarbons," Russian Journal of Organic Chemistry, vol. 39, No. 2, 2003, pp. 180-182.

* cited by examiner

*Primary Examiner* — Yong L Chu
(74) *Attorney, Agent, or Firm* — Balaram Gupta

(57) ABSTRACT

Embodiments in accordance with the present invention relate generally to a variety of norbornene derivatives exhibiting olfactive properties and are suitable as fragrance ingredients. More specifically, this invention relates to various fragrance compositions containing one or more of a compound of formula (I):

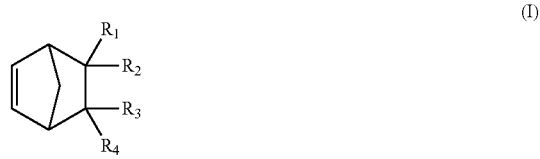

(I)

Wherein $R_1$, $R_2$, $R_3$ and $R_4$ are as defined herein. The compounds of formula (I) are useful as perfumes, colognes, and in perfume augmenting, modifying, enhancing, and imparting compositions. The compositions of this invention are therefore useful in a variety of products including perfumes, colognes, soaps, detergents, candles, air fresheners, trash bags, tissues, deodorants, lotions, skin care products, hair products, sanitary products, cleaning products, and the like.

20 Claims, No Drawings

FRAGRANCE COMPOSITIONS CONTAINING NORBORNENE DERIVATIVES

CROSS REFERENCE TO RELATED APPLICATIONS

This application claims the benefit of U.S. Provisional Application No. 62/698,453, filed Jul. 16, 2018, which is incorporated herein by reference in its entirety.

BACKGROUND OF THE INVENTION

Field of the Invention

Embodiments in accordance with the present invention relate generally to a variety of norbornene derivatives exhibiting olfactive properties and are suitable as fragrance ingredients. More specifically, this invention relates to various fragrance compositions containing a variety of functionalized norbornene (NB) compounds for use as perfumes, colognes, and in perfume augmenting, modifying, enhancing, and imparting compositions. The compositions of this invention are therefore useful in a variety of perfumed products including but not limited to perfumes, colognes, soaps, detergents, candles, air fresheners, trash bags, tissues, deodorants, lotions, skin care products, hair products, sanitary products, cleaning products, and the like.

Description of the Art

A variety of fragrance compounds are used as perfumes in the market, several of which are derived from natural sources. However, a key drawback of such natural sources is continuous sustained availability of the raw materials. Another drawback is that there is always a batch to batch variation in the quality of the products. A further drawback of such naturally occurring fragrance compounds is high cost associated with their purification because of low yield of isolation from their natural sources. It should also be noted that some of the naturally occurring fragrance compounds may be toxic to animals and people in their natural state requiring tedious methodologies for their isolation and purification. See, for example, H. M. Berven, Fragrance, Vol. 42, 46-64 (2017).

As a result, there has been a considerable research efforts to find new cost effective synthetic, non-toxic fragrance compounds and compositions that can meet the ever growing demand for such compounds/compositions. More importantly, such synthetically made fragrance compounds/compositions are expected to maintain uniform product quality with no batch to batch variations, and can be tailored to be environmentally friendly. As a result, such synthetic fragrance compounds/compositions may thus provide solution to changing environmental landscape, and may alleviate some of the environmental concerns by reducing waste generated by currently used purification processes to make naturally occurring fragrance compounds.

U.S. Pat. No. 4,119,577 discloses certain substituted norbornane perfume compositions. U.S. Pat. No. 4,374,054 discloses a variety of norbornene and norbornane carboxylic acid derivatives useful as perfumery components. U.S. Pat. No. 4,128,509 discloses a fragrance composition containing 1-(norborn-2-yl)-2-methyl-butan-3-ol, which supposedly exhibits similar odor as that of a naturally occurring mixture of α- and β-santalol, commonly found in sandalwood oil. See also, U.S. Pat. No. 4,229,600. U.S. Pat. No. 4,218,347 discloses methyl substituted or unsubstituted norbornene aldehyde carboxylic acid esters suitable as a perfuming and/or a flavoring ingredient. U.S. Pat. No. 4,351,748 discloses a series of norbornane and norbornene derivatives having epoxy carboxylic acid ester side chain, which are useful as perfuming ingredients. Finally, U.S. Pat. No. 4,132,677 discloses perfume compositions containing cyanoethylidenenorbornenes.

Thus, it is an object of this invention to provide a variety of functionalized norbornene derivatives useful as fragrance components in a variety of perfumed products and perfumery applications.

Other objects and further scope of the applicability of the present invention will become apparent from the detailed description that follows.

SUMMARY OF THE INVENTION

It has now been found that a fragrance composition can be made using a variety of functionalized norbornene compounds of formula (I). Accordingly, there is provided a fragrance composition comprising:

a) an effective amount of at least one compound of formula (I) in the form of any one of its enantiomers or a mixture thereof:

wherein:
at least one of $R_1$, $R_2$, $R_3$ and $R_4$ is selected from the group consisting of: substituted or unsubstituted $(C_3-C_8)$cycloalkyl; substituted or unsubstituted $(CR_5R_6)_a(C_3-C_8)$cycloalkyl; substituted or unsubstituted phenyl;
a group of formula (A):

$$-Z-(CO)OR \qquad (A);$$

a group of formula (B):

$$-Z-O(CO)R \qquad (B);$$

a group of formula (C):

$$-Z-O(CO)OR \qquad (C);$$

a group of formula (D):

$$-Z-CR_5((CO)OR)_2 \qquad (D); \text{ and}$$

a group of formula (E):

$$-Z-OR \qquad (E);$$

wherein:
Z is a bond or a group selected from the group consisting of:
$(CR_5R_6)_a$, $(CR_5R_6)_a-O-(CR_5R_6)_b$, $(CR_5R_6)_a-(CO)O-(CR_5R_6)_b$, $(CR_5R_6)_a-O(CO)-(CR_5R_6)_b$, $(CR_5R_6)_a-(CO)-(CR_5R_6)_b$, where a and b are integers which may be the same or different and each independently is 1 to 12;
$R_5$ and $R_6$ are the same or different and each independently selected from the group consisting of hydrogen, methyl, ethyl, linear or branched $(C_3-C_6)$alkyl, perfluoro$(C_1-C_{12})$alkyl, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl$(C_1-C_6)$alkyl, perfluoro$(C_6-C_{10})$ aryl, perfluoro($C_6$-$C_{10}$)aryl($C_1$-$C_3$)alkyl, ($C_2$-$C_6$) acyl, hydroxymethyl, hydroxyethyl and linear or branched hydroxy($C_3$-$C_6$)alkyl;

R is selected from the group consisting of hydrogen, methyl, ethyl, linear or branched ($C_3$-$C_6$)alkyl, perfluoro($C_1$-$C_{12}$)alkyl, ($C_3$-$C_{12}$)cycloalkyl, ($C_6$-$C_{12}$)bicycloalkyl, ($C_7$-$C_{14}$)tricycloalkyl, ($C_6$-$C_{10}$)aryl, ($C_6$-$C_{10}$)aryl($C_1$-$C_6$)alkyl, perfluoro($C_6$-$C_{10}$)aryl, perfluoro($C_6$-$C_{10}$)aryl($C_1$-$C_3$)alkyl, methoxy, ethoxy, linear or branched ($C_3$-$C_6$)alkoxy, perfluoro($C_1$-$C_{12}$)alkoxy, ($C_3$-$C_{12}$)cycloalkoxy, ($C_6$-$C_{12}$)bicycloalkoxy, ($C_7$-$C_{14}$)tricycloalkoxy, ($C_6$-$C_{10}$)aryloxy, ($C_6$-$C_{10}$)aryl($C_1$-$C_6$)alkoxy, ($C_2$-$C_4$)alkenyl($C_6$-$C_{10}$)aryl($C_1$-$C_6$)alkoxy, perfluoro($C_6$-$C_{10}$)aryloxy, perfluoro($C_6$-$C_{10}$)aryl($C_1$-$C_3$)alkoxy, ($C_2$-$C_6$)acyl, hydroxymethyl, hydroxyethyl and linear or branched hydroxy($C_3$-$C_6$)alkyl; and the remaining $R_1$, $R_2$, $R_3$ and $R_4$ is selected from the group consisting of hydrogen, methyl, ethyl, linear or branched ($C_3$-$C_6$)alkyl, perfluoro($C_1$-$C_{12}$)alkyl, ($C_3$-$C_{12}$)cycloalkyl, ($C_6$-$C_{12}$)bicycloalkyl, ($C_7$-$C_{14}$)tricycloalkyl, ($C_6$-$C_{10}$)aryl, ($C_6$-$C_{10}$)aryl($C_1$-$C_6$)alkyl, perfluoro($C_6$-$C_{10}$)aryl, perfluoro($C_6$-$C_{10}$)aryl($C_1$-$C_3$)alkyl, methoxy, ethoxy, linear or branched ($C_3$-$C_6$)alkoxy, perfluoro($C_1$-$C_{12}$)alkoxy, ($C_3$-$C_{12}$)cycloalkoxy, ($C_6$-$C_{12}$)bicycloalkoxy, ($C_7$-$C_{14}$)tricycloalkoxy, ($C_6$-$C_{10}$)aryloxy, ($C_6$-$C_{10}$)aryl($C_1$-$C_6$)alkoxy, perfluoro($C_6$-$C_{10}$)aryloxy, perfluoro($C_6$-$C_{10}$)aryl($C_1$-$C_3$)alkoxy, ($C_2$-$C_6$)acyl, hydroxymethyl, hydroxyethyl and linear or branched hydroxy($C_3$-$C_6$)alkyl;

with the proviso that when Z is a bond, R is not hydrogen, methyl, ethyl, linear or branched ($C_3$-$C_6$)alkyl;

b) at least one ingredient selected from the group consisting of a fragrance carrier and a fragrance base; and c) optionally at least one fragrance adjuvant.

In another aspect of this invention there is further provided a method to confer, enhance, improve or modify the odor properties of a perfuming composition or of a perfumed article, which method comprises adding to said composition or article an effective amount of at least one compound of formula (I) in the form of any one of its enantiomers or a mixture thereof.

DETAILED DESCRIPTION

The terms as used herein have the following meanings:

As used herein, the articles "a," "an," and "the" include plural referents unless otherwise expressly and unequivocally limited to one referent.

Since all numbers, values and/or expressions referring to quantities of ingredients, reaction conditions, etc., used herein and in the claims appended hereto, are subject to the various uncertainties of measurement encountered in obtaining such values, unless otherwise indicated, all are to be understood as modified in all instances by the term "about."

Where a numerical range is disclosed herein such range is continuous, inclusive of both the minimum and maximum values of the range as well as every value between such minimum and maximum values. Still further, where a range refers to integers, every integer between the minimum and maximum values of such range is included. In addition, where multiple ranges are provided to describe a feature or characteristic, such ranges can be combined. That is to say that, unless otherwise indicated, all ranges disclosed herein are to be understood to encompass any and all sub-ranges subsumed therein. For example, a stated range of from "1 to 10" should be considered to include any and all sub-ranges between the minimum value of 1 and the maximum value of 10. Exemplary sub-ranges of the range 1 to 10 include, but are not limited to, 1 to 6.1, 3.5 to 7.8, and 5.5 to 10, etc.

As used herein, the bond symbol "∿" in various structures shown below denotes that the stereochemistry at this position is not determined and may constitute all possible stereoisomers, including "exo" or "endo" isomers. Accordingly whenever a structure shown with the symbol "∿" means that it includes all possible stereoisomers at that configuration.

The expression "stereoisomers" is a general term used for all isomers of the individual molecules that differ only in the orientation of their atoms in space. Typically it includes mirror image isomers that are usually formed due to at least one asymmetric center, (enantiomers). In addition, as noted above, the compounds of formula (I) may exist in two different forms "exo" and "endo" configurations merely because of their spatial orientation. Where the compounds according to the invention possess two or more asymmetric centers, they may additionally exist as diastereoisomers, also certain individual molecules may exist as geometric isomers (cis/trans). Similarly, certain compounds of this invention may exist in a mixture of two or more structurally distinct forms that are in rapid equilibrium, commonly known as tautomers. Representative examples of tautomers include keto-enol tautomers, phenol-keto tautomers, nitroso-oxime tautomers, imine-enamine tautomers, etc. It is to be understood that all such isomers and mixtures thereof in any proportion are encompassed within the scope of the present invention.

As used herein, the expression "alkyl" means a saturated, straight-chain or branched-chain hydrocarbon substituent having the specified number of carbon atoms. Particular alkyl groups are methyl, ethyl, n-propyl, isopropyl, tert-butyl, and so on. Derived expressions such as "alkoxy", "thioalkyl", "alkoxyalkyl", "hydroxyalkyl", "alkylcarbonyl", "alkoxycarbonylalkyl", "alkoxycarbonyl", "diphenylalkyl", "phenylalkyl", "phenylcarboxyalkyl" and "phenoxyalkyl" are to be construed accordingly.

As used herein, the expression "cycloalkyl" includes all of the known cyclic groups. Representative examples of "cycloalkyl" includes without any limitation cyclopropyl, cyclobutyl, cyclopentyl, cyclohexyl, cycloheptyl, cyclooctyl, and the like. Derived expressions such as "cycloalkoxy", "cycloalkylalkyl", "cycloalkylaryl", "cycloalkylcarbonyl" are to be construed accordingly.

As used herein, the expression "perfluoroalkyl" means that all of the hydrogen atoms in said alkyl group are replaced with fluorine atoms, again having the specified number of carbon atoms. Illustrative examples include trifluoromethyl and pentafluoroethyl, and straight-chained or branched heptafluoropropyl, nonafluorobutyl, undecafluoropentyl and tridecafluorohexyl groups. Derived expression, "perfluoroalkoxy", is to be construed accordingly. It should further be noted that certain of the alkyl groups as described herein, such as for example, "alkyl" may partially be fluorinated, that is, only portions of the hydrogen atoms in said alkyl group are replaced with fluorine atoms and shall be construed accordingly.

As used herein, the expression "aryl" means substituted or unsubstituted aromatic groups such as phenyl, naphthyl, anthracenyl, and the like. Specific examples of substituted phenyl or naphthyl include o-, p-, m-tolyl, 1,2-, 1,3-, 1,4-xylyl, 1-methylnaphthyl, 2-methylnaphthyl, etc. "Substituted phenyl" or "substituted naphthyl" also include any of the possible substituents as further defined herein or one known in the art.

As used herein, the expression "arylalkyl" means that the aryl as defined herein is further attached to alkyl as defined herein. Representative examples include benzyl, phenylethyl, 2-phenylpropyl, 1-naphthylmethyl, 2-naphthylmethyl and the like.

As used herein, the expression "alkenyl" means a non-cyclic, straight or branched hydrocarbon chain having the specified number of carbon atoms and containing at least one carbon-carbon double bond, and includes ethenyl and straight-chained or branched propenyl, butenyl, pentenyl and hexenyl groups. Derived expression, "arylalkenyl" and five membered or six membered "heteroarylalkenyl" is to be construed accordingly. Illustrative examples of such derived expressions include furan-2-ethenyl, phenylethenyl, 4-methoxyphenylethenyl, and the like.

As used herein the expression "acyl" shall have the same meaning as "alkanoyl", which can also be represented structurally as "R—CO—," where R is an "alkyl" as defined herein having the specified number of carbon atoms. Additionally, "alkylcarbonyl" shall mean same as "acyl" as defined herein. Specifically, "$(C_1-C_4)$acyl" shall mean formyl, acetyl or ethanoyl, propanoyl, n-butanoyl, etc. Derived expressions such as "acyloxy" and "acyloxyalkyl" are to be construed accordingly.

"Halogen" or "halo" means chloro, fluoro, bromo, and iodo.

In a broad sense, the term "substituted" is contemplated to include all permissible substituents of organic compounds. In a few of the specific embodiments as disclosed herein, the term "substituted" means substituted with one or more substituents independently selected from the group consisting of $(C_1-C_6)$alkyl, $(C_2-C_6)$alkenyl, $(C_1-C_6)$perfluoroalkyl, phenyl, hydroxy, —$CO_2H$, an ester, an amide, $(C_1-C_6)$alkoxy, $(C_1-C_6)$thioalkyl and $(C_1-C_6)$perfluoroalkoxy. However, any of the other suitable substituents known to one skilled in the art can also be used in these embodiments.

It should be noted that any atom with unsatisfied valences in the text, schemes, examples and tables herein is assumed to have the appropriate number of hydrogen atom(s) to satisfy such valences.

By the term "fragrance" or "fragrance compound" or "fragrance composition" is meant a compound or a composition that exhibits pleasant, lasting floral, fruity, woody, spicy, nutty, herbal aroma, which is useful in the preparation of fragrance compositions and perfumed products.

By the term "effective olfactory" or "effective olfactive" or "effective odoriferous" amount of a compound is meant a sufficient amount of the compound to impart desirable sense of smell to the composition.

As used herein, the expression "fragrance carrier" or "fragrance base" means a non-toxic solvent, dispersant, excipient, adjuvant, or other material which is mixed with the compound of formula (I) as described herein in order to permit the formation of a fragrance composition, as further disclosed herein.

Accordingly, in accordance with the practice of this invention there is provided a fragrance composition comprising:

a) an effective amount of at least one compound of formula (I) in the form of any one of its enantiomers or a mixture thereof:

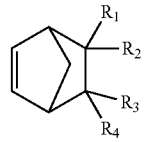

(I)

wherein:
at least one of $R_1$, $R_2$, $R_3$ and $R_4$ is selected from the group consisting of: substituted or unsubstituted $(C_3-C_8)$cycloalkyl; substituted or unsubstituted $(CR_5R_6)_a(C_3-C_8)$cycloalkyl; substituted or unsubstituted phenyl;
a group of formula (A):

$$—Z—(CO)OR \qquad (A);$$

a group of formula (B):

$$—Z—O(CO)R \qquad (B);$$

a group of formula (C):

$$—Z—O(CO)OR \qquad (C);$$

a group of formula (D):

$$—Z—CR_5((CO)OR)_2 \qquad (D);\ and$$

a group of formula (E):

$$—Z—OR \qquad (E);$$

wherein:
Z is a bond or a group selected from the group consisting of:
$(CR_5R_6)_a$, $(CR_5R_6)_a$—O—$(CR_5R_6)_b$, $(CR_5R_6)_a$—(CO)O—$(CR_5R_6)_b$, $(CR_5R_6)_a$—O(CO)—$(CR_5R_6)_b$, $(CR_5R_6)_a$—(CO)—$(CR_5R_6)_b$, where a and b are integers which may be the same or different and each independently is 1 to 12;
$R_5$ and $R_6$ are the same or different and each independently selected from the group consisting of hydrogen, methyl, ethyl, linear or branched $(C_3-C_6)$alkyl, perfluoro$(C_1-C_{12})$alkyl, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl$(C_1-C_6)$alkyl, perfluoro$(C_6-C_{10})$aryl, perfluoro$(C_6-C_{10})$aryl$(C_1-C_3)$alkyl, $(C_2-C_6)$acyl, hydroxymethyl, hydroxyethyl and linear or branched hydroxy$(C_3-C_6)$alkyl;
R is selected from the group consisting of hydrogen, methyl, ethyl, linear or branched $(C_3-C_6)$alkyl, perfluoro$(C_1-C_{12})$alkyl, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl$(C_1-C_6)$alkyl, perfluoro$(C_6-C_{10})$aryl, perfluoro$(C_6-C_{10})$aryl$(C_1-C_3)$alkyl, methoxy, ethoxy, linear or branched $(C_3-C_6)$alkoxy, perfluoro$(C_1-C_{12})$alkoxy, $(C_3-C_{12})$cycloalkoxy, $(C_6-C_{12})$bicycloalkoxy, $(C_7-C_4)$tricycloalkoxy, $(C_6-C_{10})$aryloxy, $(C_6-C_{10})$aryl$(C_1-C_6)$alkoxy, $(C_2-C_4)$alkenyl$(C_6-C_{10})$aryl$(C_1-C_6)$alkoxy, perfluoro$(C_6-C_{10})$aryloxy, perfluoro$(C_6-C_{10})$aryl$(C_1-C_3)$alkoxy, $(C_2-C_6)$acyl, hydroxymethyl, hydroxyethyl and linear or branched hydroxy$(C_3-C_6)$alkyl; and
the remaining $R_1$, $R_2$, $R_3$ and $R_4$ is selected from the group consisting of hydrogen, methyl, ethyl, linear or branched $(C_3-C_6)$alkyl, perfluoro$(C_1-C_{12})$alkyl, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl$(C_1-C_6)$alkyl, perfluoro$(C_6-C_{10})$aryl, perfluoro$(C_6-C_{10})$aryl$(C_1-C_3)$alkyl, methoxy, ethoxy, linear or branched $(C_3-C_6)$alkoxy, perfluoro$(C_1-C_{12})$alkoxy, $(C_3-C_{12})$cycloalkoxy, $(C_6-C_{12})$bicycloalkoxy, $(C_7-C_{14})$tricycloalkoxy, $(C_6-C_{10})$aryloxy, $(C_6-C_{10})$aryl$(C_1-C_6)$alkoxy, perfluoro$(C_6-C_{10})$aryloxy, perfluoro$(C_6-C_{10})$aryl$(C_1-C_3)$alkoxy, $(C_2-C_6)$ acyl, hydroxymethyl, hydroxyethyl and linear or branched hydroxy($C_3$-$C_6$)alkyl;
with the proviso that when Z is a bond, R is not hydrogen, methyl, ethyl, linear or branched ($C_3$-$C_6$)alkyl;
b) at least one ingredient selected from the group consisting of a fragrance carrier and a fragrance base; and
c) optionally at least one fragrance adjuvant.

The compounds employed in the composition of this invention are themselves known in the literature or can be prepared by any of the known methods in the art to make such or similar types of compounds. In general, the compounds of formula (I) can be prepared by employing cyclopentadiene and a suitable substituted olefin of formula (IA) and reacting them together under Diels Alder reaction conditions to form a compound of formula (I) as summarized in Scheme I.

Scheme I

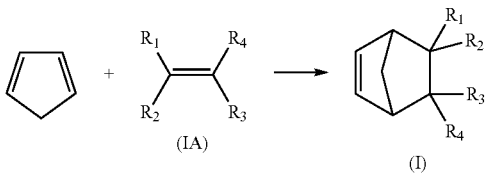

The Diels Alder reaction is generally carried out at higher temperatures in a closed reactor by mixing suitable amounts of cyclopentadiene with a desirable substituted olefin of formula (IA) which facilitates the (4π+2π) addition of the double bonds to form the compound of formula (I). Generally, such reactions are carried out in an autoclave at higher temperatures and optionally in the presence of a suitable solvent. The resulting product is generally a mixture of exo- and endo-isomers of formula (I). These isomers may exhibit different olfactive properties and therefore, in some embodiments only one of the isomers may be more suitable in the fragrance compositions of this inventions. In some other embodiments both exo and endo isomers may be employed equally readily to form the olfactively effective fragrance compositions of this invention.

In some embodiments the fragrance composition according to the present invention contains one or more compounds of formula (I), wherein said at least one of $R_1$, $R_2$, $R_3$ and $R_4$ is substituted or unsubstituted ($C_3$-$C_8$)cycloalkyl and the remaining $R_1$, $R_2$, $R_3$ and $R_4$ is selected from the group consisting of hydrogen, methyl, ethyl, linear or branched propyl, linear or branched butyl, $CF_3$, cyclohexyl, phenyl, benzyl, phenethyl, $C_6F_5$, methoxy, ethoxy, phenoxy, hydroxymethyl and hydroxyethyl.

Non-limiting examples of such compounds of formula (I) that can be employed in the fragrance composition of this invention include all geometric and stereoisomers of the following:

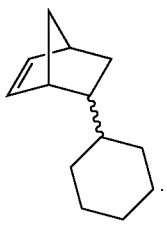

5-cyclohexylbicyclo[2.2.1]hept-2-ene (NBCyHex)

In yet some other embodiments the fragrance composition according to the present invention encompasses a compound of formula (I), wherein said at least one of $R_1$, $R_2$, $R_3$ and $R_4$ is a group of formula (A):

—Z—(CO)OR     (A);

wherein:
Z is a bond or a group selected from the group consisting of:
($CH_2$)$_a$, ($CH_2$)$_a$—O—($CH_2$)$_b$, where a and b are integers which may be the same or different and each independently is 1 to 4;
R is selected from the group consisting of methyl, ethyl, linear or branched propyl, linear or branched butyl, $CF_3$, cyclohexyl, phenyl, benzyl, phenethyl, $C_6F_5$, adamantyl and methyladamantanyl;
and
the remaining $R_1$, $R_2$, $R_3$ and $R_4$ is selected from the group consisting of hydrogen, hydrogen, methyl, ethyl, linear or branched propyl, linear or branched butyl, $CF_3$, cyclohexyl, phenyl, benzyl, phenethyl, $C_6F_5$, methoxy, ethoxy, phenoxy, hydroxymethyl and hydroxyethyl.

Representative examples of such compounds of the formula (I) within the scope of this embodiment, without any limitation, including all possible geometric and stereoisomers, may be selected from the group consisting of:

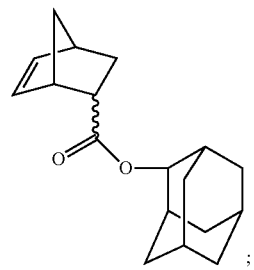

2-adamantan-2-yl bicyclo[2.2.1]hept-5-ene-2-carboxylate (AdEsNB)

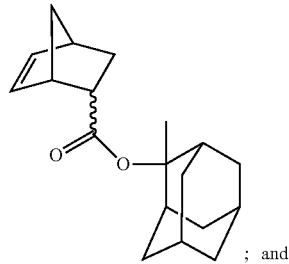

; and 2-methyladamantan-2-yl bicyclo[2.2.1]hept-5-ene-2-carboxylate (MeAdEsNB)

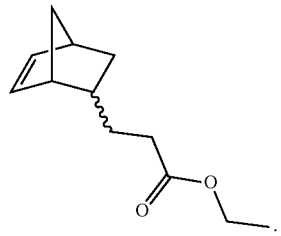

ethyl 3-(bicyclo[2.2.1]hept-5-ene-2-yl)propanoate (EPEsNB)

In yet some other embodiments, the fragrance composition according to the present invention encompasses a compound of formula (I), wherein said at least one of $R_1$, $R_2$, $R_3$ and $R_4$ is a group of formula (B):

—Z—O(CO)R     (B);

wherein:

Z is a bond or a group selected from the group consisting of:
- $(CH_2)_a$, $(CH_2)_a$—O—$(CH_2)_b$, where a and b are integers which may be the same or different and each independently is 1 to 4;

R is selected from the group consisting of methyl, ethyl, linear or branched propyl, linear or branched butyl, cyclohexyl, phenyl, benzyl, phenethyl, and —CH=CH—$C_6H_4$—$OCH_3$; and the remaining $R_1$, $R_2$, $R_3$ and $R_4$ is selected from the group consisting of hydrogen, hydrogen, methyl, ethyl, linear or branched propyl, linear or branched butyl, $CF_3$, cyclohexyl, phenyl, benzyl, phenethyl, $C_6F_5$, methoxy, ethoxy, phenoxy, hydroxymethyl and hydroxyethyl.

Representative examples of such compounds of the formula (I) within the scope of this embodiment, without any limitation, including all possible geometric and stereoisomers, may be selected from the group consisting of:

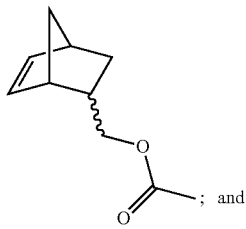

(bicyclo[2.2.1]hept-5-en-2-yl)methyl acetate (NBMeOAc)

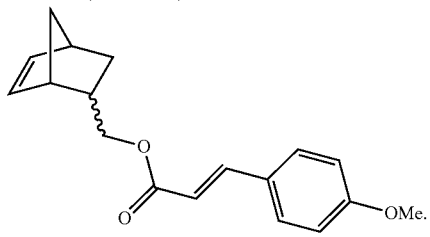

(bicyclo[2.2.1]hept-5-en-2-yl)methyl 3-(4-methoxyphenyl)acrylate (NBMeOCinnamate)

In yet some other embodiments, the fragrance composition according to the present invention encompasses a compound of formula (I), wherein said at least one of $R_1$, $R_2$, $R_3$ and $R_4$ is a group of formula (C):

—Z—O(CO)OR       (C);

wherein:

Z is a bond or a group selected from the group consisting of:
- $(CH_2)_a$, $(CH_2)_a$—O—$(CH_2)_b$, where a and b are integers which may be the same or different and each independently is 1 to 4;

R is selected from the group consisting of methyl, ethyl, linear or branched propyl, linear or branched butyl, cyclohexyl, phenyl, benzyl and phenethyl; and the remaining $R_1$, $R_2$, $R_3$ and $R_4$ is selected from the group consisting of hydrogen, hydrogen, methyl, ethyl, linear or branched propyl, linear or branched butyl, $CF_3$, cyclohexyl, phenyl, benzyl, phenethyl, $C_6F_5$, methoxy, ethoxy, phenoxy, hydroxymethyl and hydroxyethyl.

Representative examples of such compounds of the formula (I) within the scope of this embodiment, without any limitation, including all possible geometric and stereoisomers, may be selected from the group consisting of:

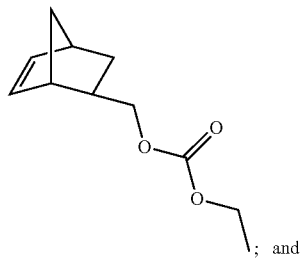

(bicyclo[2.2.1]hept-5-en-2-yl)methyl ethyl carbonate (NBEtCarb)

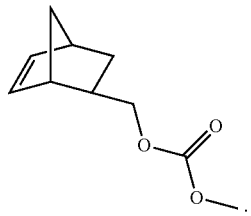

(bicyclo[2.2.1]hept-5-en-2-yl)methyl methyl carbonate (NBMeCarb)

In yet some other embodiments, the fragrance composition according to the present invention encompasses a compound of formula (I), wherein said at least one of $R_1$, $R_2$, $R_3$ and $R_4$ is a group of formula (D):

—Z—$CR_5$((CO)OR)$_2$       (D);

wherein:

Z is a bond or a group selected from the group consisting of:
- $(CH_2)_a$, $(CH_2)_a$—O—$(CH_2)_b$, where a and b are integers which may be the same or different and each independently is 1 to 4;

$R_5$ is selected from the group consisting of hydrogen, methyl and ethyl;

R is selected from the group consisting of methyl, ethyl, linear or branched propyl, linear or branched butyl, cyclohexyl, phenyl, benzyl and phenethyl; and the remaining $R_1$, $R_2$, $R_3$ and $R_4$ is selected from the group consisting of hydrogen, hydrogen, methyl, ethyl, linear or branched propyl, linear or branched butyl, $CF_3$, cyclohexyl, phenyl, benzyl, phenethyl, $C_6F_5$, methoxy, ethoxy, phenoxy, hydroxymethyl and hydroxyethyl.

Representative examples of such compounds of the formula (I) within the scope of this embodiment, without any limitation, including all possible geometric and stereoisomers, may be selected from the group consisting of:

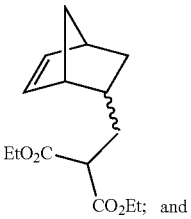

diethyl 2-((bicyclo[2.2.1]hept-5-en-2-yl)methyl)malonate (NBdiEtMalonate)

-continued

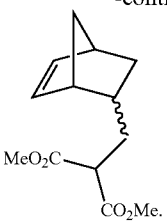

dimethyl 2-((bicyclo[2.2.1]hept-5-en-2-yl)
methyl)malonate

In yet some other embodiments, the fragrance composition according to the present invention encompasses a compound of formula (I), wherein said at least one of $R_1$, $R_2$, $R_3$ and $R_4$ is a group of formula (E):

—Z—OR    (E);

wherein:
Z is a bond or a group selected from the group consisting of:
$C(CH_3)_2$, $(CH_2)_a$, $(CH_2)_a$—O—$(CH_2)_b$, where a and b are integers which may be the same or different and each independently is 1 to 4;
R is selected from the group consisting of methyl, ethyl, linear or branched propyl, linear or branched butyl, cyclohexyl, phenyl, benzyl and phenethyl; and
the remaining $R_1$, $R_2$, $R_3$ and $R_4$ is selected from the group consisting of hydrogen, hydrogen, methyl, ethyl, linear or branched propyl, linear or branched butyl, $CF_3$, cyclohexyl, phenyl, benzyl, phenethyl, $C_6F_5$, methoxy, ethoxy, phenoxy, hydroxymethyl and hydroxyethyl.

Representative examples of such compounds of the formula (I) within the scope of this embodiment, without any limitation, including all possible geometric and stereoisomers, may be selected from the group consisting of:

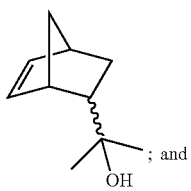

2-(bicyclo[2.2.1]hept-5-en-2-yl)
propane-2-ol (NBXOH)

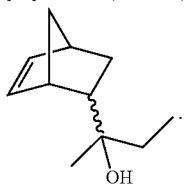

2-(bicyclo[2.2.1]hept-5-en-2-yl)
butan-2-ol

Various other compounds similar to compounds of formula (I) can also be employed in the fragrance compositions of this invention. For example, the compounds of formula (I), wherein, either $R_1$ and $R_2$ or $R_3$ and $R_4$ combined with the carbon atom to which they are attached to form a carbocyclic ($C_3$-$C_7$) ring optionally containing one or more heteroatoms selected from oxygen or nitrogen, and in addition a keto group so as to form either a lactone or a lactam ring. Representative examples of such spiro compounds may be enumerated as follows:

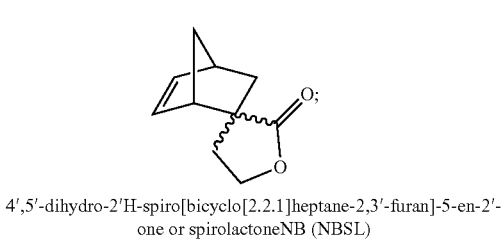

4′,5′-dihydro-2′H-spiro[bicyclo[2.2.1]heptane-2,3′-furan]-5-en-2′-
one or spirolactoneNB (NBSL)

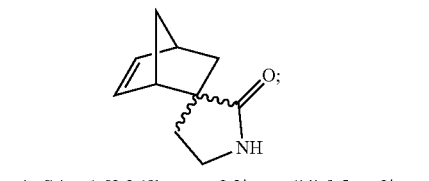

spiro[bicyclo[2.2.1]heptane-2,3′-pyrrolidin]-5-en-2′-one

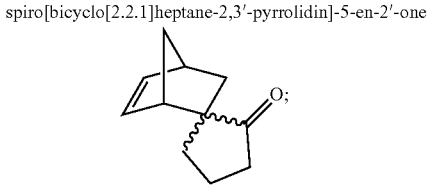

spiro[bicyclo[2.2.1]heptane-2,1′-cyclopentan]-5-en-2′-one

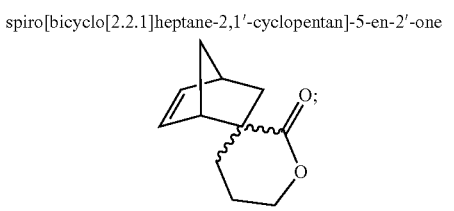

5′,6′-dihyrdo-2′H,4′H-spiro[bicyclo[2.2.1]heptane-2,3′-pyran]-5-en-
2′-one

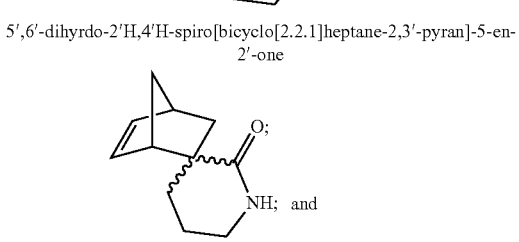

spiro[bicyclo[2.2.1]heptane-2,3′-piperidin]-5-en-2′-one

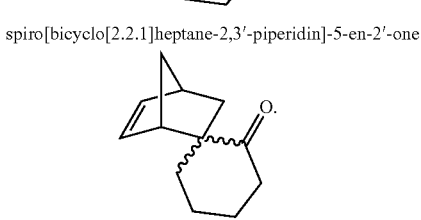

spiro[bicyclo[2.2.1]heptane-2,1′-cyclohexan]-5-en-2′-one

In general, the fragrance compositions in accordance with the present invention encompass at least one of the above described compounds of formula (I) and if needed additional one or more compounds of formula (I) in order to provide the intended olfactive property to such embodiments that are appropriate and desirable for the use for which such embodiments are directed, thus such embodiments are tailorable to a variety of specific applications.

For example, as already discussed above, proper combination of distinctive monomers of formula (I) makes it possible to tailor a composition having the desirable olfactive property having utility in different fragrance compositions. That is, depending upon the intended applications, including perfumed products, such as, perfumes, colognes, soaps, detergents, candles, air fresheners, trash bags, tissues, deodorants, lotions, skin care products, hair products, sanitary products, cleaning products, etc., the compositions can be tailored to provide such intended benefits.

Accordingly, there is further provided a perfuming composition comprising i) at least one compound of formula (I), as defined herein; ii) at least one ingredient selected from the group consisting of a perfumery carrier and a perfumery base; and iii) optionally at least one perfumery adjuvant.

In some other embodiments, there is also provided a perfuming consumer product comprising: i) at least one compound of formula (I), as defined herein; and ii) a perfumery consumer base.

Any of the known perfumery consumer base that provide the intended benefit for such compositions can be employed in the perfuming consumer product according to the present invention. Exemplary perfumery consumer base include but not limited to a perfume, a fabric care product, a body-care product, an air care product or a home care product.

In a further non-limiting examples of a perfuming consumer product according to the present invention encompasses a perfumery consumer base selected from a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

In an additional aspect of this invention there is further provided a method to confer, enhance, improve or modify the odor properties of a perfuming composition or of a perfumed article, which method comprises adding to said composition or article an effective amount of at least one compound of formula (I), as defined herein, including the form of any one of its enantiomers or a mixture thereof.

Any one or more of the specific compounds of formula (I) as described hereinabove can be used in the method according to the present invention.

In a further embodiment of this invention, the composition contains any of the fragrance carrier and a fragrance base and optionally at least one fragrance adjuvant that would bring about the intended benefit. Generally, such suitable fragrance carriers include a suitable gaseous or liquid carriers, among others. Gaseous carriers are generally used in aerosol compositions and are inert to compositions of this invention. Non-limiting examples of gaseous carriers include air, nitrogen, carbon dioxide, any suitable organic solvent, water, and the like.

The compounds of formula (I) may be used alone, as mixtures thereof, in combination with a fragrance carrier and/or a fragrance base material. As used herein, the "fragrance base material" includes all known odorant molecules selected from the extensive range of natural products, and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, and other auxiliary agents commonly used in the art.

As used herein, "fragrance composition" means any composition comprising at least one compound of formula (I) and a fragrance base material and/or a fragrance carrier. For example, a diluent conventionally used in conjunction with odorants, such as dipropylene glycol (DPG), isopropyl myristate (IPM), triethyl citrate (TEC), alcohol (e.g. ethanol), and the like may be used as fragrance carrier.

Non-limiting examples of known odorant molecules, which may be combined with the compounds of formula (I) as herein defined include the following: essential oils and extracts, e.g. castoreum, costus root oil, oak moss absolute, geranium oil, tree moss absolute, basil oil, fruit oils, such as bergamot oil and mandarine oil, myrtle oil, palmarose oil, patchouli oil, petitgrain oil, jasmine oil, rose oil, sandalwood oil, wormwood oil, lavender oil or ylang-ylang oil; alcohols, e.g. cinnamic alcohol, cis-3-hexenol, citronellol, EBANOL™, eugenol, farnesol, geraniol, SUPER MUGUET™, linalool, menthol, nerol, phenylethyl alcohol, rhodinol, SANDALORE™, terpineol or TIMBEROL™. Various known aldehydes and ketones used as fragrance compounds and/or fragrance enhancing compounds, including but not limited to AZURONE® [7-(3-methylbutyl)-1,5-benzodioxepin-3-one], anisaldehyde, α-amylcinnamaldehyde, GEORGYWOOD™, hydroxycitronellal, ISO E® Super, ISORALDEINE®, HEDIONE®, LILIAL®, maltol, methyl cedryl ketone, methylionone, verbenone, or vanillin. Various known ether and acetals used as fragrance compounds and/or fragrance enhancing compounds, including but not limited to AMBROX®, geranyl methyl ether, rose oxide, or SPIRAMBRENE®. Various known esters and lactones used as fragrance compounds and/or fragrance enhancing compounds, including but not limited to benzyl acetate, cedryl acetate, γ-decalactone, HELVETOLIDE®, γ-undecalactone or vetivenyl acetate; macrocycles, e.g. Ambrettolide, ethylene brassylate or EXALTOLIDE®. Various known heterocycles used as fragrance compounds and/or fragrance enhancing compounds, including but not limited to isobutylchinoline.

The compounds according to formula (I) may be used in a broad range of perfumed products, e.g. in any field of fine and functional perfumery, such as perfumes, air care products, household products, laundry products, body care products and cosmetics. The compounds can be employed in widely varying amounts, depending upon the specific application and on the nature and quantity of other odorant ingredients, if employed. The proportion is typically from 0.1 to 10 weight percent of the application. In one embodiment, compounds of the present invention may be employed in a fabric softener in an amount of from 0.001 to 0.1 weight percent. In another embodiment, compounds of the present invention may be used in fine perfumery in amounts from 0.01 to 20 weight percent (e.g. up to about 10 weight percent). In some other embodiments, between 0.01 and 5 weight percent. It should be noted however that these values are given only by way of example, since the experienced perfumer may also achieve effects or may create intended benefit with lower or higher concentrations.

The compounds as described hereinabove may be employed in a consumer product base simply by directly mixing at least one compound of formula (I), or a fragrance composition with the consumer product base, or they may, in an earlier step, be entrapped with an entrapment material, for example, polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the consumer product base.

Thus, the invention additionally provides a method of manufacturing a perfumed product, comprising the incorporation of a compound of formula (I), as a fragrance ingredient, either by directly admixing the compound to the consumer product base or by admixing a fragrance composition comprising a compound of formula (I), which may then be mixed with a consumer product base, using conventional techniques and methods. Through the addition of an olfactory acceptable amount of at least one compound of the present invention as hereinabove described the odor notes of a consumer product base will be improved, enhanced, or modified.

Thus, the invention furthermore provides a method for improving, enhancing or modifying a consumer product base by means of the addition thereto of an olfactively acceptable amount of at least one compound of formula (I).

The invention also provides a perfumed product comprising: a) as odorant at least one compound of formula (I); and b) a consumer product base.

As used herein, "consumer product base" means a composition for use as a consumer product to fulfill specific actions, such as cleaning, softening, and caring or the like. Examples of such products include fine perfumery, e.g. perfume and eau de toilette; fabric care, household products and personal care products such as laundry care detergents, rinse conditioner, personal cleansing composition, detergent for dishwasher, surface cleaner; laundry products, e.g. softener, bleach, detergent; body-care products, e.g. shampoo, shower gel; air care products and cosmetics, e.g. deodorant, vanishing cream or lotion. This list of products is given by way of illustration, and is not to be regarded as being in any way limiting.

Substances suitable for use herein as co-ingredients or flavoring adjuvants are well known in the art for such use, being extensively described in the relevant literature. In addition, one of skill in the art will readily appreciate that any such material be non-toxic especially in a household product and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising broadly stabilizers, thickeners, surface active agents, conditioners, other flavorants and flavor intensifiers.

Stabilizer compounds include preservatives, for example, sodium chloride; antioxidants, such as for example, calcium and sodium ascorbate, ascorbic acid, butylated hydroxyanisole (mixture of 2- and 3-tertiary-butyl-4-hydroxyanisole), butylated hydroxytoluene (2,6-di-tertiary-butyl-4-methylphenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectins and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, turmeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include aldehydes, esters, natural oils, alcohols, sulfides, ketones, lactones, carboxylic acids and hydrocarbons such as heliotropin, terpinenol-4, benzaldehyde, phenyl acetaldehyde, benzyl formate, cis-3-hexenyl benzoate, methyl hexanoate, hexanal, eucalyptol, acetaldehyde, ethyl acetate, ethyl butyrate, turpentine gum oil, limonene, gum camphor, isobornyl acetate, borneol, cinnamic aldehyde, cuminic aldehyde, furfural, methyl cinnamate, cassia oil, parahydroxybenzyl acetate, dimethyl sulfide, alphaionone, acetic acid, isobutyl acetate, acetone, butyric acid, formic acid, valeric acid, amyl acetate, amyl butyrate, anethol, benzyl salicylate, diacetyl, dimethyl anthranilate, ethyl methylphenylglycidate, ethyl succinate, ethyl valerate, cis-3-hexen-1-ol, 2-hexenyl acetate, 2-hexenyl butyrate, hexyl butyrate, 4-(p-hydroxyphenyl)-2-butanone, betaionone, isobutyl cinnamate, lemon essential oil, methyl butyrate, methyl caproate, methyl disulfide, methyl p-naphthyl ketone, orris butter, rose absolute, terpenyl acetate, gamma-undecalactone, vanilla and alcohol.

The specific flavoring adjuvant selected for use may be either solid or liquid depending upon the desired physical form of the ultimate product, i.e., and should, (i) be organoleptically compatible with the compounds of formula (I) of this invention by not covering or spoiling the organoleptic properties (aroma and/or taste) thereof; (ii) be non-reactive with the compounds of formula (I) of this invention and (iii) be capable of providing an environment in which the compounds of formula (I) of this invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the ultimate product to which the flavor and/or aroma are to be imparted, modified, altered or enhanced.

The following examples are detailed descriptions of methods of preparation and use of compositions of the present invention. The detailed preparations fall within the scope of, and serve to exemplify, the more generally described methods of preparation set forth above. The examples are presented for illustrative purposes only, and are not intended as a restriction on the scope of the invention.

EXAMPLES

The following abbreviations have been used hereinbefore and hereafter in describing some of the compounds, instruments and/or methods employed to illustrate certain of the embodiments of this invention:

NBCyHex—5-cyclohexylbicyclo[2.2.1]hept-2-ene;
MeAdEsNB—2-methyladamantan-2-yl bicyclo[2.2.1]hept-5-ene-2-carboxylate;
EPEsNB—ethyl 3-(bicyclo[2.2.1]hept-5-en-2-yl)propanoate;
NBMeOAc—(bicyclo[2.2.1]hept-5-en-2-yl)methyl acetate;
NBMeOCinnamate—(bicyclo[2.2.1]hept-5-en-2-yl)methyl 3-(4-methoxyphenyl)acrylate;
NBEtCarb—(bicyclo[2.2.1]hept-5-en-2-yl)methyl ethyl carbonate;
NBdiEtMalonate—diethyl 2-((bicyclo[2.2.1]hept-5-en-2-yl)methyl)malonate; and
NBXOH—2-(bicyclo[2.2.1]hept-5-en-2-yl)propan-2-ol.

Various compounds of formula (I) as described herein are either commercially available or can be readily prepared following the procedures as described herein or following the procedures as reported in literature, see for example, U.S. Pat. No. 4,374,054.

Example 1

Olfactive Evaluations

A panel of three perfumers evaluated various compounds of formula (I). Each of the panelists tested the samples essentially under same atmospheric conditions. All materials were olfactively evaluated neat from glass jars. Liquid materials were also evaluated on blotter for a 24 hour period. Evaluations included odor type, odor strength and odor characteristics. The results from these evaluations are summarized in Table 1.

TABLE 1

| Sample | Perfumer 1 | Perfumer 2 | Perfumer 3 |
| --- | --- | --- | --- |
| NBCyHex | Moderately strong buttery, nutty odor with mint overtones | Herbaceous, mushroomy, minty jasmine like odor | Floral note with consistent fresh freesia and lilly odor |
| MeAdEsNB | Moderately strong spicy pine odor | Moderate citrus (limey), piney and earth odor | Fresh sweet spicy ginger note |
| EPEsNB | Moderately strong sweet fruity odor with green, woody and fatty notes | Fruity, ethereal citrus odor | Clean, consistent fruity odor. not very diffusive but good tenacity |
| NBMeOAc | Nice fruity odor, apple with woody notes, very diffusive | Fruity odor with banana, green, chamomile notes | Fruity green banana odor, very diffusive |
| NBMeOCinnamate | Moderately strong nice sweet, fruity odor with floral elements | Fruity odor with cherry-almond, marzipan notes | Bubble gum, sugary sweet odor, also displays a red berry note |
| NBEtCarb | A nutty, fruity odor with mint elements | Fruity floral odor with green, banana, violet notes | Fruity pineapple fatty waxy note with an interesting floral aspect |
| NBdiEtMalonate | Moderately strong sweet, fruity odor with nice green, melon and woody notes | Fruity odor with apple notes | Ethereal "witch hazel" initial note followed by pleasant apple floral character |
| NBXOH | Nice earthy, green odor with touches of mint and wood | Strong limey odor | Earthy gassy odor |

Example 2

Personal Care/Air Care Product Formulation

A personal care product such as hand soaps, hand moisturizer, and the like or air care product such as air fresheners can be made using the formulation as set forth below.

A suitable combination of five to ten parts by weight of a compound of formula (I) as summarized in Example 1 or a mixture of one or more compounds as listed therein can be combined with a mixture containing ten to fifteen parts by weight of hexyl cinnamic aldehyde, six to ten parts by weight of benzyl propionate, one to two parts by weight of isoeugenol, one to two parts by weight of diethyl phthalate, six to ten parts by weight of linalool, six to ten parts by weight of benzyl acetate, six to ten parts by weight of benzyl salicylate, six to ten parts by weight of must ambrette and any other suitable fragrance agent to form a formulation which can be used in any of the personal care products and/or air care products.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A fragrance composition comprising:
   a) an effective amount of at least one compound of formula (I) in the form of any one of its enantiomers or a mixture thereof:

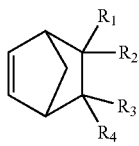

(I)

wherein:
at least one of $R_1$, $R_2$, $R_3$ and $R_4$ is selected from the group consisting of:
substituted or unsubstituted $(C_3-C_8)$cycloalkyl; substituted or unsubstituted $(CR_5R_6)_a(C_3-C_8)$cycloalkyl; substituted or unsubstituted phenyl;
a group of formula (A):

—Z—(CO)OR (A); and a group of formula (D):

—Z—CR$_5$((CO)OR)$_2$ (D);

wherein:
Z is a bond or a group selected from the group consisting of:
$(CR_5R_6)_a$, $(CR_5R_6)_a$—O—$(CR_5R_6)_b$, $(CR_5R_6)_a$—(CO)O—$(CR_5R_6)_b$, $(CR_5R_6)_a$—O(CO)—$(CR_5R_6)_b$, $(CR_5R_6)_a$—(CO)—$(CR_5R_6)_b$, where a and b are integers which may be the same or different and each independently is 1 to 12;
$R_5$ and $R_6$ are the same or different and each independently selected from the group consisting of hydrogen, methyl, ethyl, linear or branched $(C_3-C_6)$alkyl, perfluoro$(C_1-C_{12})$alkyl, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl$(C_1-C_6)$alkyl, perfluoro$(C_6-C_{10})$aryl, perfluoro$(C_6-C_{10})$aryl$(C_1-C_3)$alkyl, $(C_2-C_6)$acyl, hydroxymethyl, hydroxyethyl and linear or branched hydroxy$(C_3-C_6)$alkyl;
R is selected from the group consisting of hydrogen, methyl, ethyl, linear or branched $(C_3-C_6)$alkyl, perfluoro$(C_1-C_{12})$alkyl, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl$(C_1-C_6)$alkyl, perfluoro$(C_6-C_{10})$aryl, perfluoro$(C_6-C_{10})$aryl$(C_1-C_3)$alkyl, methoxy, ethoxy, linear or branched $(C_3-C_6)$alkoxy, perfluoro$(C_1-C_{12})$alkoxy, $(C_3-C_{12})$cycloalkoxy, $(C_6-C_{12})$bicycloalkoxy, $(C_7-C_{14})$tricycloalkoxy, $(C_6-C_{10})$aryloxy, $(C_6-C_{10})$aryl$(C_1-C_6)$alkoxy, $(C_2-C_4)$alkenyl$(C_6-C_{10})$aryl$(C_1-C_6)$alkoxy, perfluoro$(C_6-C_{10})$aryloxy, perfluoro$(C_6-C_{10})$aryl$(C_1-C_3)$alkoxy, $(C_2-C_6)$acyl, hydroxymethyl, hydroxyethyl and linear or branched hydroxy$(C_3-C_6)$alkyl; and
the remaining $R_1$, $R_2$, $R_3$ and $R_4$ is selected from the group consisting of hydrogen, methyl, ethyl, linear or branched $(C_3-C_6)$alkyl, perfluoro$(C_1-C_{12})$alkyl, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl$(C_1-C_6)$alkyl, perfluoro$(C_6-C_{10})$aryl, perfluoro$(C_6-C_{10})$aryl$(C_1-C_3)$alkyl, methoxy, ethoxy, linear or branched $(C_3-C_6)$alkoxy, perfluoro$(C_1-C_{12})$alkoxy, $(C_3-C_{12})$cycloalkoxy, $(C_6-C_{12})$bicycloalkoxy, $(C_7-C_{14})$tricycloalkoxy, $(C_6-C_{10})$aryloxy, $(C_6-C_{10})$aryl$(C_1-C_6)$alkoxy, perfluoro$(C_6-C_{10})$aryloxy, perfluoro$(C_6-C_{10})$aryl$(C_1-C_3)$alkoxy, $(C_2-C_6)$acyl, hydroxymethyl, hydroxyethyl and linear or branched hydroxy$(C_3-C_6)$alkyl;
with the proviso that when Z is a bond, R is not hydrogen, methyl, ethyl, or linear or branched $(C_3-C_6)$alkyl;
b) at least one ingredient selected from the group consisting of a fragrance carrier and a fragrance base; and
c) optionally at least one fragrance adjuvant.

2. The fragrance composition according to claim 1, wherein said at least one of $R_1$, $R_2$, $R_3$ and $R_4$ is substituted or unsubstituted $(C_3-C_8)$cycloalkyl and the remaining $R_1$, $R_2$, $R_3$ and $R_4$ is selected from the group consisting of hydrogen, methyl, ethyl, linear or branched propyl, linear or branched butyl, $CF_3$, cyclohexyl, phenyl, benzyl, phenethyl, $C_6F_5$, methoxy, ethoxy, phenoxy, hydroxymethyl and hydroxyethyl.

3. The fragrance composition according to claim 2, wherein said compound of formula (I) is

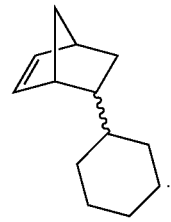

5-cyclohexylbicyclo[2.2.1]hept-2-ene (NBCyHex)

4. The fragrance composition according to claim 1, wherein said at least one of $R_1$, $R_2$, $R_3$ and $R_4$ is a group of formula (A):

—Z—(CO)OR (A);

wherein:
Z is a bond or a group selected from the group consisting of:
$(CH_2)_a$, $(CH_2)_a$—O—$(CH_2)_b$, where a and b are integers which may be the same or different and each independently is 1 to 4;
R is selected from the group consisting of methyl, ethyl, linear or branched propyl, linear or branched butyl, $CF_3$, cyclohexyl, phenyl, benzyl, phenethyl, $C_6F_5$ and methyladamantanyl; and
the remaining $R_1$, $R_2$, $R_3$ and $R_4$ is selected from the group consisting of hydrogen, methyl, ethyl, linear or branched propyl, linear or branched butyl, $CF_3$, cyclohexyl, phenyl, benzyl, phenethyl, $C_6F_3$, methoxy, ethoxy, phenoxy, hydroxymethyl and hydroxyethyl.

5. The fragrance composition according to claim 4, wherein said compound of formula (I) is selected from the group consisting of:

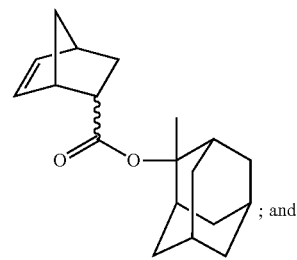

; and 2-methyladamantan-2-yl bicyclo[2.2.1]hept-5-ene-2-carboxylate
(MeAdEsNB)

-continued

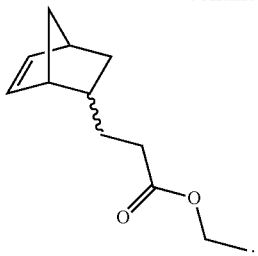

ethyl 3-(bicyclo[2.2.1]hept-5-en-2-yl)
propanoate (EPEsNB)

6. A fragrance composition comprising:
a) an effective amount of at least one compound of formula (I) in the form of any one of its enantiomers or a mixture thereof:

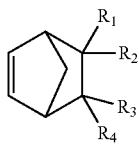
(I)

wherein
at least one of $R_1$, $R_2$, $R_3$ and $R_4$ is a group of formula (B):

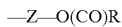
—Z—O(CO)R (B);

wherein:
Z is selected from the group consisting of:
$(CH_2)_a$, and $(CH_2)_a$—O—$(CH_2)_b$, where a and b are integers which may be the same or different and each independently is 1 to 4;
R is selected from the group consisting of cyclohexyl, phenyl, benzyl, phenethyl, and —CH=CH—$C_6H_4$—$OCH_3$; and
the remaining $R_1$, $R_2$, $R_3$ and $R_4$ is selected from the group consisting of hydrogen, methyl, ethyl, linear or branched propyl, linear or branched butyl, $CF_3$, cyclohexyl, phenyl, benzyl, phenethyl, $C_6F_5$, methoxy, ethoxy, phenoxy, hydroxymethyl and hydroxyethyl,
b) at least one ingredient selected from the group consisting of a fragrance carrier and a fragrance base; and
c) optionally at least one fragrance adjuvant.

7. The fragrance composition according to claim 6, wherein said compound of formula (I) is:

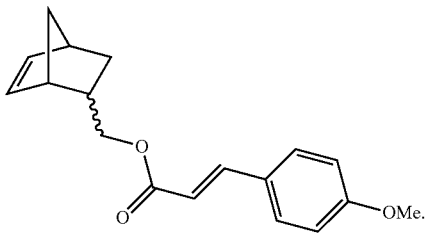

(bicyclo[2.2.1]hept-5-en-2-yl)methyl 3-(4-methoxyphenyl)acrylate (NBMeOCinnamate)

8. The fragrance composition according to claim 1, wherein said at least one of $R_1$, $R_2$, $R_3$ and $R_4$ is a group of formula (D):

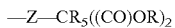
—Z—$CR_5$((CO)OR)$_2$ (D);

wherein:
Z is a bond or a group selected from the group consisting of:
$(CH_2)_a$, $(CH_2)_a$—O—$(CH_2)_b$, where a and b are integers which may be the same or different and each independently is 1 to 4;
$R_5$ is selected from the group consisting of hydrogen, methyl and ethyl;
R is selected from the group consisting of methyl, ethyl, linear or branched propyl, linear or branched butyl, cyclohexyl, phenyl, benzyl and phenethyl; and
the remaining $R_1$, $R_2$, $R_3$ and $R_4$ is selected from the group consisting of hydrogen, methyl, ethyl, linear or branched propyl, linear or branched butyl, $CF_3$, cyclohexyl, phenyl, benzyl, phenethyl, $C_6F_5$, methoxy, ethoxy, phenoxy, hydroxymethyl and hydroxyethyl.

9. The fragrance composition according to claim 8, wherein said compound of formula (I) is selected from the group consisting of:

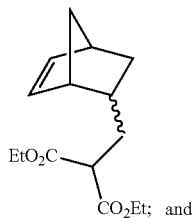

diethyl 2-((bicyclo[2.2.1]hept-5-en-2-yl)methyl)malonate

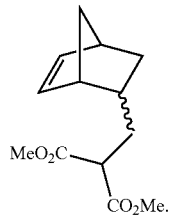

dimethyl 2-((bicyclo[2.2.1]hept-5-en-2-yl)methyl)malonate

10. A fragrance composition comprising:
a) an effective amount of at least one compound of formula (I) in the form of any one of its enantiomers or a mixture thereof:

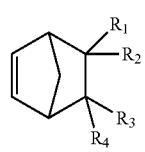
(I)

wherein
at least one of $R_1$, $R_2$, $R_3$ and $R_4$ is a group of formula (E):

—Z—OR (E);

wherein:
Z is $(CR_5R_6)_a$ where a is 1 to 4 and each $R_5$ and $R_6$ is independently selected from the group consisting of methyl and ethyl;
R is selected from the group consisting of hydrogen, methyl, ethyl, linear or branched propyl, linear or branched butyl, cyclohexyl, phenyl, benzyl and phenethyl; and the remaining $R_1$, $R_2$, $R_3$ and $R_4$ is selected from the group consisting of hydrogen, methyl, ethyl, linear or branched propyl, linear or branched butyl, $CF_3$, cyclohexyl, phenyl, benzyl, phenethyl, $C_6F_5$, methoxy, ethoxy, phenoxy, hydroxymethyl and hydroxyethyl;
b) at least one ingredient selected from the group consisting of a fragrance carrier and a fragrance base; and
c) optionally at least one fragrance adjuvant.

11. The fragrance composition according to claim 10, wherein said compound of formula (I) is selected from the group consisting of:

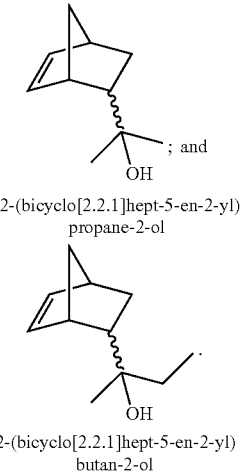

2-(bicyclo[2.2.1]hept-5-en-2-yl)propane-2-ol 2-(bicyclo[2.2.1]hept-5-en-2-yl)butan-2-ol 12. A perfuming composition comprising i) at least one compound of formula (I), as defined in claim 1; ii) at least one ingredient selected from the group consisting of a perfumery carrier and a perfumery base; and iii) optionally at least one perfumery adjuvant.

13. A perfuming consumer product comprising: i) at least one compound of formula (I), as defined in claim 1; and ii) a perfumery consumer base.

14. A perfuming consumer product according to claim 13, wherein said perfumery consumer base is a perfume, a fabric care product, a body-care product, an air care product or a home care product.

15. A perfuming consumer product according to claim 13, wherein said perfumery consumer base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

16. A method to confer, enhance, improve or modify the odor properties of a perfuming composition or of a perfumed article, which method comprises adding to said composition or article an effective amount of at least one compound of formula (I) in the form of any one of its enantiomers or a mixture thereof:

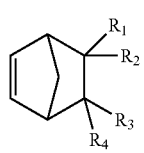
(I)

wherein:
at least one of $R_1$, $R_2$, $R_3$ and $R_4$ is selected from the group consisting of:
substituted or unsubstituted $(C_3-C_8)$cycloalkyl; substituted or unsubstituted $(CR_5R_6)_a(C_3-C_8)$cycloalkyl; substituted or unsubstituted phenyl;
a group of formula (A):

—Z—(CO)OR    (A); and a group of formula (D):

—Z—$CR_5$((CO)OR)$_2$    (D);

wherein:
Z is a bond or a group selected from the group consisting of:
$(CR_5R_6)_a$, $(CR_5R_6)_a$—O—$(CR_5R_6)_b$, $(CR_5R_6)_a$—(CO)O—$(CR_5R_6)_b$, $(CR_5R_6)_a$—O(CO)—$(CR_5R_6)_b$, $(CR_5R_6)_a$—(CO)—$(CR_5R_6)_b$, where a and b are integers which may be the same or different and each independently is 1 to 12;
$R_5$ and $R_6$ are the same or different and each independently selected from the group consisting of hydrogen, methyl, ethyl, linear or branched $(C_3-C_6)$alkyl, perfluoro$(C_1-C_{12})$alkyl, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl$(C_1-C_6)$alkyl, perfluoro$(C_6-C_{10})$aryl, perfluoro$(C_6-C_{10})$aryl$(C_1-C_3)$alkyl, $(C_2-C_6)$acyl, hydroxymethyl, hydroxyethyl and linear or branched hydroxy$(C_3-C_6)$alkyl;
R is selected from the group consisting of hydrogen, methyl, ethyl, linear or branched $(C_3-C_6)$alkyl, perfluoro$(C_1-C_{12})$alkyl, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl$(C_1-C_6)$alkyl, perfluoro$(C_6-C_{10})$aryl, perfluoro$(C_6-C_{10})$aryl$(C_1-C_3)$alkyl, methoxy, ethoxy, linear or branched $(C_3-C_6)$alkoxy, perfluoro$(C_1-C_{12})$alkoxy, $(C_3-C_{12})$cycloalkoxy, $(C_6-C_{12})$bicycloalkoxy, $(C_7-C_{14})$tricycloalkoxy, $(C_6-C_{10})$aryloxy, $(C_6-C_{10})$aryl$(C_1-C_6)$alkoxy, $(C_2-C_4)$alkenyl$(C_6-C_{10})$aryl$(C_1-C_6)$alkoxy, perfluoro$(C_6-C_{10})$aryloxy, perfluoro$(C_6-C_{10})$aryl$(C_1-C_3)$alkoxy, $(C_2-C_6)$acyl, hydroxymethyl, hydroxyethyl and linear or branched hydroxy$(C_3-C_6)$alkyl; and
the remaining $R_1$, $R_2$, $R_3$ and $R_4$ is selected from the group consisting of hydrogen, methyl, ethyl, linear or branched $(C_3-C_6)$alkyl, perfluoro$(C_1-C_{12})$alkyl, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl$(C_1-C_6)$alkyl, perfluoro$(C_6-C_{10})$aryl, perfluoro$(C_6-C_{10})$aryl$(C_1-C_3)$alkyl, methoxy, ethoxy, linear or branched $(C_3-C_6)$alkoxy, perfluoro$(C_1-C_{12})$alkoxy, $(C_3-C_{12})$cycloalkoxy, $(C_6-C_{12})$bicycloalkoxy, $(C_7-C_{14})$tricycloalkoxy, $(C_6-C_{10})$aryloxy, $(C_6-C_{10})$aryl$(C_1-C_6)$alkoxy, perfluoro$(C_6-C_{10})$aryloxy, perfluoro$(C_6-C_{10})$aryl$(C_1-C_3)$alkoxy, $(C_2-C_6)$acyl, hydroxymethyl, hydroxyethyl and linear or branched hydroxy$(C_3-C_6)$alkyl.

17. The method according to claim 16, wherein said compound of formula (I) is selected from the group consisting of:

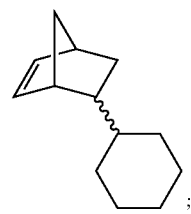

5-cyclohexylbicyclo[2.2.1]hept-2-ene (NBCyHex)

-continued

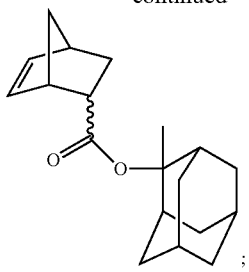

2-methyladamantan-2-yl bicyclo[2.2.1]hept-5-ene-2-carboxylate (MeAdEsNB)

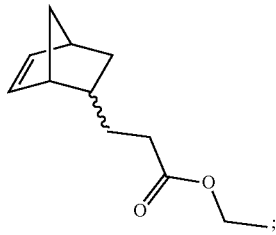

ethyl 3-(bicyclo[2.2.1]hept-5-en-2-yl)propanoate (EPEsNB)

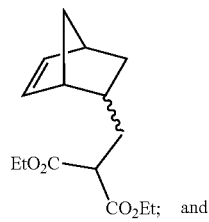

diethyl 2-((bicyclo[2.2.1]hept-5-en-2-yl)methyl)malonate

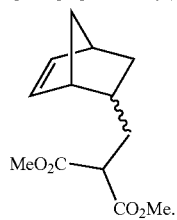

dimethyl 2-((bicyclo[2.2.1]hept-5-en-2-yl)methyl)malonate

18. The method according to claim 16, wherein said compound of formula (I) is selected from the group consisting of:

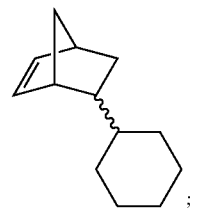

5-cyclohexylbicyclo[2.2.1]hept-2-ene (NBCyHex)

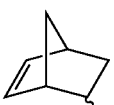

ethyl 3-(bicyclo[2.2.1]hept-5-en-2-yl)propanoate (EPEsNB)

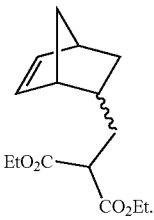

diethyl 2-((bicyclo[2.2.1]hept-5-en-2-yl)methyl)malonate

19. A perfuming composition comprising i) at least one compound of formula (I), as defined in claim 6; ii) at least one ingredient selected from the group consisting of a perfumery carrier and a perfumery base; and iii) optionally at least one perfumery adjuvant.

20. A perfuming composition comprising i) at least one compound of formula (I), as defined in claim 10; ii) at least one ingredient selected from the group consisting of a perfumery carrier and a perfumery base; and iii) optionally at least one perfumery adjuvant.

* * * * *